(12) United States Patent
Sosnowski et al.

(10) Patent No.: US 11,484,689 B2
(45) Date of Patent: Nov. 1, 2022

(54) MEDICAL DEVICE DELIVERY SYSTEM

(71) Applicant: Covidien LP, Mansfield, MA (US)

(72) Inventors: Stephen A. Sosnowski, Vista, CA (US); David G. Matsuura, Del Mar, CA (US); Philip J. Simpson, Escondido, CA (US); Belinko K. Matsuura, Encinitas, CA (US); Jeffrey J. Loos, Carlsbad, CA (US)

(73) Assignee: COVIDIEN LP, Mansfield, MA (US)

( * ) Notice: Subject to any disclaimer, the term of this patent is extended or adjusted under 35 U.S.C. 154(b) by 124 days.

(21) Appl. No.: 15/929,580

(22) Filed: May 11, 2020

(65) Prior Publication Data

US 2020/0269016 A1 Aug. 27, 2020

Related U.S. Application Data

(63) Continuation of application No. 15/274,068, filed on Sep. 23, 2016, now Pat. No. 10,688,282.

(Continued)

(51) Int. Cl.
*A61M 25/01* (2006.01)
*A61B 17/12* (2006.01)
(Continued)

(52) U.S. Cl.
CPC ......... *A61M 25/01* (2013.01); *A61B 17/1214* (2013.01); *A61B 17/12118* (2013.01);
(Continued)

(58) Field of Classification Search
CPC .......... A61F 2/011; A61F 2/95; A61F 2/9522; A61F 2/966; A61F 2/9661; A61F 2/9662; A61F 2/2427; A61F 2/243; A61F 2/2433; A61F 2/2436; A61F 2002/9665; A61M 25/0023; A61M 25/0052; A61M 25/0082; A61M 25/01; A61M 25/0108;
(Continued)

(56) References Cited

U.S. PATENT DOCUMENTS

| 4,631,054 A | * 12/1986 | Kim ..................... A61J 15/0007 604/528 |
| 5,312,415 A | 5/1994 | Palermo |

(Continued)

FOREIGN PATENT DOCUMENTS

| CN | 102188300 A | 9/2011 |
| CN | 105578998 B | 9/2017 |

(Continued)

*Primary Examiner* — Kathleen S Holwerda
*Assistant Examiner* — Kankindi Rwego
(74) *Attorney, Agent, or Firm* — Fortem IP LLP

(57) ABSTRACT

A medical device delivery system can be used to advance a medical device to a target area within a patient's vasculature. The system can comprise a catheter, a support sheath, and a core member coupled to a medical device. The core member can be used to longitudinally advanced or retracting medical device within a lumen of the support sheath. The support sheath can be advanced within the catheter until a distal end of the support sheath contacts or abuts a reduced diameter section of the catheter lumen. Thereafter, the core member can be advanced into the catheter lumen toward the target area.

19 Claims, 11 Drawing Sheets

Related U.S. Application Data

(60) Provisional application No. 62/233,252, filed on Sep. 25, 2015.

(51) Int. Cl.
*A61F 2/966* (2013.01)
*A61M 25/00* (2006.01)
*A61F 2/95* (2013.01)
*A61M 25/06* (2006.01)

(52) U.S. Cl.
CPC ......... *A61F 2/966* (2013.01); *A61M 25/0023* (2013.01); *A61M 25/0082* (2013.01); *A61M 25/0606* (2013.01); *A61B 2017/1205* (2013.01); *A61F 2/9522* (2020.05); *A61F 2002/9665* (2013.01)

(58) Field of Classification Search
CPC .............. A61M 25/0606; A61M 25/09; A61M 2025/09125; A61M 2025/09175; A61M 2025/09183; A61M 25/0009; A61M 25/0068; A61M 25/007; A61M 25/0102; A61M 25/0152; A61B 17/12118; A61B 17/1214; A61B 17/3468; A61B 2017/1205
USPC ...................................................... 623/1.11
See application file for complete search history.

(56) References Cited

U.S. PATENT DOCUMENTS

| | | | |
|---|---|---|---|
| 5,876,450 A * | 3/1999 | Johlin, Jr. | A61M 27/008 623/1.13 |
| 5,902,282 A | 5/1999 | Balbierz | |
| 5,904,651 A | 5/1999 | Swanson et al. | |
| 6,015,424 A | 1/2000 | Rosenbluth et al. | |
| 6,254,612 B1 | 7/2001 | Hieshima | |
| 6,416,530 B2 | 7/2002 | Devries et al. | |
| 6,533,751 B2 * | 3/2003 | Cragg | A61M 25/00 604/264 |
| 6,658,288 B1 | 12/2003 | Hayashi | |
| 7,300,458 B2 | 11/2007 | Henkes et al. | |
| 7,458,974 B1 | 12/2008 | Hayashi et al. | |
| 8,016,853 B2 | 9/2011 | Griffen et al. | |
| 8,114,148 B2 | 2/2012 | Atanasoska et al. | |
| 8,236,046 B2 | 8/2012 | Weber | |
| 8,556,927 B2 | 10/2013 | Dehnad | |
| 8,603,014 B2 | 12/2013 | Alleman et al. | |
| 8,668,732 B2 | 3/2014 | Scheuermann et al. | |
| 8,715,339 B2 | 5/2014 | Atanasoska et al. | |
| 8,771,299 B2 | 7/2014 | Diamant et al. | |
| 8,837,800 B1 | 9/2014 | Bammer et al. | |
| 9,119,656 B2 | 9/2015 | Bose et al. | |
| 9,126,018 B1 | 9/2015 | Garrison | |
| 9,211,132 B2 | 12/2015 | Bowman | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2002/0120297 A1 | 8/2002 | Shadduck | |
| 2003/0055448 A1 | 3/2003 | Lee et al. | |
| 2003/0217794 A1 | 11/2003 | Boylan et al. | |
| 2004/0068314 A1 | 4/2004 | Jones et al. | |
| 2005/0119723 A1 | 6/2005 | Peacock | |
| 2006/0271153 A1 * | 11/2006 | Garcia | A61F 2/95 623/1.11 |
| 2007/0270942 A1 | 11/2007 | Thomas | |
| 2008/0082107 A1 * | 4/2008 | Miller | A61B 17/221 606/127 |
| 2008/0132906 A1 | 6/2008 | Rasmussen | |
| 2008/0183272 A1 | 7/2008 | Wood et al. | |
| 2008/0234723 A1 | 9/2008 | Buiser et al. | |
| 2008/0262489 A1 | 10/2008 | Steinke et al. | |
| 2009/0270974 A1 | 10/2009 | Berez et al. | |
| 2010/0008970 A1 | 1/2010 | Obrien et al. | |
| 2010/0145380 A1 | 6/2010 | Schmutz et al. | |
| 2011/0238041 A1 | 9/2011 | Lim et al. | |
| 2011/0245775 A1 | 10/2011 | Tekulve | |
| 2013/0030461 A1 | 1/2013 | Marks et al. | |
| 2013/0281788 A1 | 10/2013 | Garrison | |
| 2013/0304185 A1 | 11/2013 | Newell et al. | |
| 2014/0276074 A1 | 9/2014 | Warner | |
| 2014/0343595 A1 | 11/2014 | Monstadt et al. | |
| 2015/0066129 A1 | 3/2015 | Nageswaran et al. | |
| 2015/0359547 A1 | 12/2015 | Vale et al. | |
| 2015/0374479 A1 | 12/2015 | Vale | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151183 A1 | 6/2016 | Nishigishi | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0296690 A1 | 10/2016 | Kume et al. | |
| 2016/0302808 A1 | 10/2016 | Loganathan et al. | |
| 2016/0375180 A1 | 12/2016 | Anzai | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0185614 A1 | 7/2018 | Garrison et al. | |

FOREIGN PATENT DOCUMENTS

| | | |
|---|---|---|
| EP | 2543345 A1 | 1/2013 |
| EP | 2319575 B1 | 11/2013 |
| JP | 2011147791 A | 8/2011 |
| JP | 2014004219 A | 1/2014 |
| JP | 2018118132 A | 8/2018 |
| KR | 20180102877 A | 9/2018 |
| WO | 9748435 | 12/1997 |
| WO | 2009105710 A1 | 8/2009 |
| WO | 2013071173 A1 | 5/2013 |
| WO | 2014041428 A2 | 3/2014 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |

(56) References Cited

FOREIGN PATENT DOCUMENTS

| WO | 2018137030 A1 | 8/2018 |
|----|---------------|--------|
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

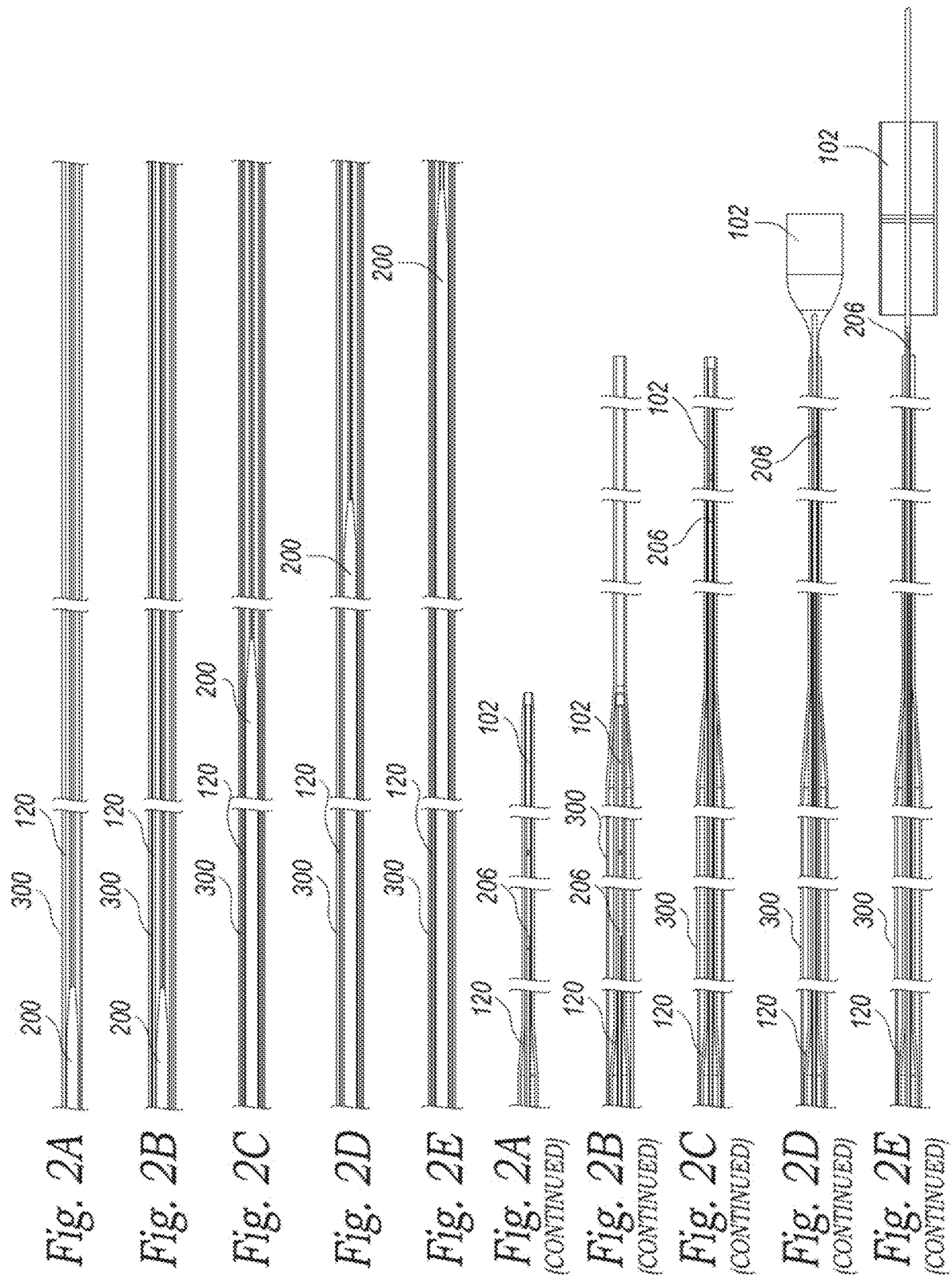

MEDICAL DEVICE DELIVERY SYSTEM

CROSS-REFERENCE TO RELATED APPLICATION(S)

The present application is a continuation of U.S. application Ser. No. 15/274,068, filed Sep. 23, 2016, which claims the benefit of and priority under 35 U.S.C. § 119(e) to U.S. Provisional Patent Application No. 62/233,252, filed Sep. 25, 2015, the disclosures of which are incorporated herein by reference in their entireties.

FIELD

The present application generally relates to medical device delivery systems, in particular systems and methods for delivering expandable implants to tortuous vessels of the vasculature.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neuro-vasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

At least one aspect of the disclosure provides methods and apparatuses for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm. Additionally, such an occluding device can allow adequate blood flow to be provided to adjacent structures such that those structures, whether they are branch vessels or oxygen demanding tissues, are not deprived of the necessary blood flow.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination with each other or one or more other independent clauses, to form an independent embodiment. The other clauses can be presented in a similar manner. The following is a non-limiting summary of some embodiments presented herein:

Clause 1. A medical device delivery system for advancing a medical device to a target area within a patient's vasculature, the system comprising: a catheter having proximal and distal sections and a lumen having an inner shoulder separating the proximal and distal sections, the catheter lumen having a larger diameter in the proximal section than in the distal section; a support sheath having proximal and distal sections and a lumen having an inner shoulder separating the proximal and distal sections, the sheath lumen having a larger diameter in the proximal section than in the distal section, the sheath being advanceable within the catheter lumen of the catheter proximal section to contact a distal end portion of the sheath against the catheter inner shoulder to stabilize the sheath within the catheter; and a core member having proximal and distal sections, an outer shoulder separating the proximal and distal sections, and a stent engagement portion in the distal section for removably engaging a stent to the core member, the distal section cross-sectional profile being less than the sheath distal section diameter to allow the stent and core member distal section to be advanced within the sheath distal section until the outer shoulder contacts the sheath inner shoulder.

Clause 2. The system of Clause 1, wherein the catheter distal section lumen diameter is about equal to the sheath distal section lumen diameter.

Clause 3. The system of Clause 2, wherein the cross-sectional profile of the core member proximal section is greater than the catheter distal section lumen diameter and the sheath distal section lumen diameter.

Clause 4. The system of Clause 1, wherein the catheter proximal section has an outer diameter of at least 0.030 inches, and the catheter distal section has an outer diameter of less than 0.020 inches.

Clause 5. The system of Clause 4, wherein the catheter proximal section has an outer diameter of at least 0.033 inches, and the catheter distal section has an outer diameter of less than 0.018 inches.

Clause 6. The system of Clause 5, wherein the catheter proximal section has an outer diameter of about 0.035 inches, and the catheter distal section has an outer diameter of about 0.017 inches.

Clause 7. The system of Clause 1, wherein the catheter lumen steps down to a smaller diameter at the inner shoulder between the proximal and distal sections.

Clause 8. The system of Clause 1, wherein the catheter lumen tapers at the inner shoulder between the proximal and distal sections.

Clause 9. The system of Clause 8, wherein the catheter lumen tapers conically in a distal direction.

Clause 10. The system of Clause 8, wherein the sheath distal end portion tapers conically in a distal direction to permit the sheath distal end portion to self-center along a longitudinal axis of the catheter when urged into contact against the catheter inner shoulder.

Clause 11. The system of Clause 1, wherein the sheath lumen tapers at the inner shoulder between the proximal and distal sections.

Clause 12. The system of Clause 1, wherein the sheath lumen steps down to a smaller diameter at the inner shoulder between the proximal and distal sections.

Clause 13. The system of Clause 1, wherein the sheath proximal section has a larger outer diameter than sheath distal section.

Clause 14. The system of Clause 1, wherein the core member distal section has a length greater than the combined length of the introducer sheath distal section and the catheter distal section.

Clause 15. The system of Clause 1, wherein the core member tapers at the outer shoulder between the proximal and distal sections.

Clause 16. The system of Clause 1, wherein the core member steps down to a smaller diameter at the outer shoulder between the proximal and distal sections.

Clause 17. The system of Clause 1, wherein the cross-sectional profile of the core member proximal section is larger than the catheter distal section lumen diameter and the sheath distal section lumen diameter.

Clause 18. The system of Clause 1, wherein the stent engagement portion of the core member comprises a longitudinal member and a plurality of stiff filaments extending radially from the longitudinal member and engaging an inner luminal surface of the stent.

Clause 19. The system of Clause 18, wherein the stiff filaments comprise bristles.

Clause 20. The system of Clause 1, wherein the stent engagement portion of the core member comprises a shaft that extends into a lumen of the stent and a filament wrapped around the stent to secure the stent to the shaft.

Clause 21. The system of Clause 20, wherein the filament is wrapped around only a proximal portion of the stent.

Clause 22. The system of Clause 20, wherein the filament comprises a polypropylene filament.

Clause 23. The system of Clause 20, wherein the support sheath distal section inner wall holds the wrapped filament in place against an outer surface of the stent when the stent is located in the support sheath distal section.

Clause 24. The system of Clause 20, wherein the filament comprises proximal and distal end portions, the filament proximal end portion being coupled to the core member, the filament distal end portion being unsecured to the stent to permit the filament distal end portion to move freely upon expansion of the stent.

Clause 25. The system of Clause 20, wherein the catheter distal section lumen diameter and the sheath distal section lumen diameter are diametrically larger than a cross-sectional profile of the filament wrapped around the stent by less than a diameter of the filament.

Clause 26. The system of Clause 1, wherein the stent engagement portion of the core member comprises a plurality of protrusions for engaging the stent.

Clause 27. The system of Clause 1, wherein when the stent is coupled to the core member via the stent engagement portion, the core member does not extend distally of the stent.

Clause 28. An introducer sheath for a medical device delivery system, the sheath comprising: a proximal section, a distal section, and a lumen extending from the proximal section to the distal section, the proximal section having a first lumen diameter, the distal section having a second lumen diameter less than the first lumen diameter; and an outer shoulder separating the proximal and distal sections whereat the first lumen diameter decreases to the second lumen diameter.

Clause 29. The sheath of Clause 28, wherein the first lumen diameter is between about 0.025 inches and about 0.035 inches.

Clause 30. The sheath of Clause 28, wherein the second lumen diameter is between about 0.015 inches and about 0.020 inches.

Clause 31. The sheath of Clause 28, wherein the sheath proximal section has a length of at least 100 cm, and the sheath distal section has a length of at least 30 cm.

Clause 32. The sheath of Clause 28, wherein the sheath proximal section has a larger outer diameter than sheath distal section.

Clause 33. The sheath of Clause 28, wherein a distal end portion of the sheath tapers conically in a distal direction.

Clause 34. The sheath of Clause 28, wherein the sheath lumen tapers at the inner shoulder between the proximal and distal sections.

Clause 35. The sheath of Clause 28, wherein the sheath lumen steps down to a smaller diameter at the inner shoulder between the proximal and distal sections.

Clause 36. A core assembly for a medical device delivery system comprising the sheath of Clause 28 and a core member positioned within the sheath lumen.

Clause 37. A medical device delivery system comprising the core assembly of Clause 36 and a support catheter having a lumen where into the core assembly can be inserted.

Clause 38. A core member of a medical device delivery system, the core member comprising: a proximal section having a first cross-sectional profile; a distal section having a second cross-sectional profile; an outer shoulder separating the proximal and distal sections whereat the first cross-sectional profile decreases to the second cross-sectional profile; and a stent engagement portion coupled to the distal section.

Clause 39. The core member of Clause 38, wherein the core member proximal section comprises a solid core elongate wire having a tapered distal tip, and wherein the core member distal section comprises a tubular member coupled to the distal tip of the core member proximal section.

Clause 40. The core member of Clause 39, wherein the stent engagement portion comprises a proximal tip extending into the tubular member.

Clause 41. The core member of Clause 38, wherein the core member comprises a continuous piece of material.

Clause 42. The core member of Clause 38, further comprising a stent coupled to the stent engagement portion.

Clause 43. The core member of Clause 38, wherein the core member distal section has a length greater than the combined length of a distal section of the sheath distal section and a distal section of the catheter.

Clause 44. The core member of Clause 38, wherein the core member distal section has a length of at least 30 cm.

Clause 45. The core member of Clause 38, wherein the core member distal section has a length of between about 30 cm and about 50 cm.

Clause 46. The core member of Clause 38, wherein the core member tapers at the outer shoulder between the proximal and distal sections.

Clause 47. The core member of Clause 38, wherein the core member steps down to a smaller diameter at the outer shoulder between the proximal and distal sections.

Clause 48. The core member of Clause 38, wherein the cross-sectional profile of the core member proximal section has a diameter of at least 0.027 inches.

Clause 49. The core member of Clause 38, wherein the cross-sectional profile of the core member proximal section has a diameter of between about 0.027 inches and about 0.040 inches.

Clause 50. The core member of Clause 38, wherein the cross-sectional profile of the core member distal section has a diameter of no more than 0.020 inches.

Clause 51. The core member of Clause 38, wherein the cross-sectional profile of the core member distal section has a diameter of between about 0.015 inches and about 0.020 inches.

Clause 52. The core member of Clause 38, wherein the stent engagement portion of the core member comprises a longitudinal member and a plurality of bristles extending radially from the longitudinal member and engaging an inner luminal surface of a stent.

Clause 53. The core member of Clause 38, wherein the stent engagement portion of the core member comprises a shaft that extends into a lumen of a stent and a filament wrapped around the stent to secure the stent against the shaft.

Clause 54. The core member of Clause 53, wherein the filament is wrapped around only a proximal portion of the stent.

Clause 55. The core member of Clause 53, wherein the filament comprises proximal and distal end portions, the filament proximal end portion being coupled to the core member stent engagement portion, the filament distal end portion being unsecured to the stent to permit the filament distal end portion to move freely upon expansion of the stent.

Clause 56. The core member of Clause 53, wherein a diameter of a distal section of the catheter lumen and a diameter of a distal section of the sheath lumen are diametrically larger than a cross-sectional profile of the filament wrapped around the stent by less than a diameter of the filament.

Clause 57. The core member of Clause 38, wherein the stent engagement portion of the core member comprises a plurality of protrusions for engaging the stent.

Clause 58. The core member of Clause 38, wherein when a stent is coupled to the core member stent engagement portion, the core member does not extend distally of the stent.

Clause 59. The core member of Clause 38, wherein the core member stent engagement portion comprises a shaft having a diameter less than a diameter of the core member distal section.

Clause 60. A core assembly for a medical device delivery system comprising the core member of Clause 38 and an introducer sheath having a lumen where into the core member can be inserted.

Clause 61. A medical device delivery system comprising the core assembly of Clause 60 and a support catheter having a lumen where into the core assembly can be inserted.

Clause 62. A core assembly for a medical device delivery system, the assembly comprising: an introducer sheath having proximal and distal sections, a lumen, and an inner shoulder extending radially within the lumen at an intersection of the proximal and distal sections, the lumen having a first diameter in the proximal section and a second diameter, less than the first diameter, in the distal section; and a core member having proximal and distal sections, an outer shoulder separating the proximal and distal sections, and a stent engagement portion at the distal section for coupling a stent thereto, the core member distal section being positioned within the sheath lumen along sheath distal section and proximal to a distal end of the sheath in a first position, wherein a cross-sectional profile of the core member distal section is less than the lumen diameter of the sheath distal section to allow core member distal section and a stent supported thereon to be advanced within the sheath distal section until the outer shoulder converges toward the sheath inner shoulder such that the core member distal section extends beyond a distal end of the sheath in a second position.

Clause 63. The assembly of Clause 62, wherein a distal end of the sheath is positioned adjacent to a distal end of the core member in the first position.

Clause 64. The assembly of Clause 62, wherein the sheath inner shoulder is spaced apart from the core member outer shoulder in the first and second positions.

Clause 65. The assembly of Clause 64, wherein the sheath inner shoulder is spaced apart from the core member outer shoulder by between about 30 cm and about 60 cm in the first position.

Clause 66. The assembly of Clause 64, wherein the sheath inner shoulder is spaced apart from the core member outer shoulder by between about 0 cm and about 30 cm in the second position.

Clause 67. The assembly of Clause 62, wherein the core member outer shoulder moves by between about 25 cm and about 35 cm relative to the sheath inner shoulder when moving from the first position to the second position.

Clause 68. The assembly of Clause 62, wherein a distal end portion of the sheath tapers conically in a distal direction.

Clause 69. The assembly of Clause 62, wherein the sheath inner shoulder tapers conically in a distal direction.

Clause 70. The assembly of Clause 62, wherein the core member outer shoulder tapers conically in a distal direction.

Clause 71. The assembly of Clause 62, further comprising a stent coupled to the stent engagement portion, wherein a cross-sectional profile of the stent engagement portion and the stent is less than the second diameter of the sheath lumen to permit travel of the stent engagement portion and stent within the sheath distal section.

Clause 72. The assembly of Clause 62, wherein when a stent is coupled to the core member stent engagement portion, the core member does not extend distally of the stent.

Clause 73. A medical device delivery system comprising the core assembly of Clause 62 and a support catheter having a lumen wherein the core assembly can be positioned.

Clause 74. The system of Clause 73, wherein the sheath is advanceable within the catheter lumen of the catheter proximal section to contact a distal end portion of the sheath against an inner shoulder of the catheter to stabilize the sheath within the catheter lumen.

Clause 75. A core assembly for a medical device delivery system, the assembly comprising: an introducer sheath having proximal and distal sections, and a lumen, the lumen having a first diameter in the proximal section and a second diameter, less than the first diameter, in the distal section; and a core member having proximal and distal sections, and a stent engagement portion at the distal section for coupling a stent thereto, the core member distal section being positioned within the sheath lumen along sheath distal section and proximal to a distal end of the sheath in a first position, the core member being distally advanceable by between about 30 cm to about 60 cm from the first position such that the core member distal section extends beyond a distal end of the sheath in a second position.

Clause 76. The assembly of Clause 75, wherein the sheath further comprises an inner shoulder extending radially within the lumen at an intersection of the sheath proximal and distal sections, and the core member further comprises an outer shoulder separating the core member proximal and distal sections, the core member being advanceable within the sheath distal section until the outer shoulder converges toward the sheath inner shoulder until reaching the second position.

Clause 77. The assembly of Clause 76, wherein the sheath inner shoulder is spaced apart from the core member outer shoulder in the first and second positions.

Clause 78. The assembly of Clause 76, wherein the sheath inner shoulder is spaced apart from the core member outer shoulder by between about 30 cm and about 60 cm in the first position.

Clause 79. The assembly of Clause 76, wherein the sheath inner shoulder is spaced apart from the core member outer shoulder by between about 0 cm and about 30 cm in the second position.

Clause 80. The assembly of Clause 76, wherein the core member outer shoulder moves by between about 25 cm and about 35 cm relative to the sheath inner shoulder when moving from the first position to the second position.

Clause 81. The assembly of Clause 76, wherein the sheath inner shoulder tapers conically in a distal direction.

Clause 82. The assembly of Clause 76, wherein the core member outer shoulder tapers conically in a distal direction.

Clause 83. The assembly of Clause 75, wherein a cross-sectional profile of the core member distal section is less than the lumen diameter of the sheath distal section to allow core member distal section and a stent supported thereon to be advanceable together within the sheath distal section.

Clause 84. The assembly of Clause 75, wherein a distal end of the sheath is positioned adjacent to a distal end of the core member in the first position.

Clause 85. The assembly of Clause 75, wherein a distal end portion of the sheath tapers conically in a distal direction.

Clause 86. The assembly of Clause 75, further comprising a stent coupled to the stent engagement portion, wherein a cross-sectional profile of the stent engagement portion and the stent is less than the second diameter of the sheath lumen to permit travel of the stent engagement portion and stent within the sheath distal section.

Clause 87. The assembly of Clause 75, wherein when a stent is coupled to the core member stent engagement portion, the core member does not extend distally of the stent.

Clause 88. A medical device delivery system comprising the core assembly of Clause 75 and a support catheter having a lumen wherein the core assembly can be positioned.

Clause 89. The system of Clause 88, wherein the sheath is advanceable within the catheter lumen of the catheter proximal section to contact a distal end portion of the sheath against an inner shoulder of the catheter to stabilize the sheath within the catheter lumen.

Clause 90. A medical device delivery system, comprising: a support catheter having proximal and distal sections and a lumen having an inner shoulder separating the proximal and distal sections, the catheter lumen having a larger diameter in the proximal section than in the distal section; and an introducer sheath having a distal section and a lumen extending therethrough, the sheath being advanceable within the catheter lumen of the catheter proximal section to contact a distal end portion of the sheath against the catheter inner shoulder to stabilize the sheath within the catheter.

Clause 91. The system of Clause 90, wherein the catheter distal section lumen diameter is about equal to the sheath distal section lumen diameter.

Clause 92. The system of Clause 91, wherein a cross-sectional profile of the sheath distal section is greater than the catheter distal section lumen diameter.

Clause 93. The system of Clause 90, wherein the catheter lumen steps down to a smaller diameter at the inner shoulder between the proximal and distal sections.

Clause 94. The system of Clause 90, wherein the catheter lumen tapers at the inner shoulder between the proximal and distal sections.

Clause 95. The system of Clause 94, wherein the catheter lumen tapers conically in a distal direction.

Clause 96. The system of Clause 94, wherein the sheath distal end portion tapers conically in a distal direction to permit the sheath distal end portion to self-center along a longitudinal axis of the catheter when urged into contact against the catheter inner shoulder.

Clause 97. The system of Clause 90, wherein the catheter proximal section has an outer diameter of at least 0.030 inches, and the catheter distal section has an outer diameter of less than 0.020 inches.

Clause 98. The system of Clause 97, wherein the catheter proximal section has an outer diameter of at least 0.033 inches, and the catheter distal section has an outer diameter of less than 0.018 inches.

Clause 99. The system of Clause 98, wherein the catheter proximal section has an outer diameter of about 0.035 inches, and the catheter distal section has an outer diameter of about 0.017 inches.

Clause 100. The system of Clause 90, wherein the sheath lumen has a larger diameter in the proximal section than in the distal section.

Clause 101. A medical device delivery system, the system comprising: a catheter having proximal and distal sections, and an inner lumen having a larger inner diameter in the proximal section than in the distal section; and a loading assembly comprising: a support sheath having a distal section and a lumen extending through the distal section; and a core assembly comprising a core member and a stent engaged by the core member; the core assembly slidably received in the support sheath with the stent positioned in the support sheath lumen in the support sheath distal section such that the stent is movable along the support sheath distal section via the core member; wherein the loading assembly is removably positioned, or removably positionable, within the catheter proximal section with a distal end of the support sheath distal section adjoining a proximal end of the catheter distal section such that the stent can be advanced distally into the catheter distal section from the support sheath distal section.

Clause 102. The system of Clause 101, wherein, when the loading assembly is positioned in the catheter proximal section, the support sheath distal section and the catheter distal section together form a common lumen having a substantially constant diameter and extending from the support sheath distal section to a distal end opening of the catheter.

Clause 103. The system of Clause 102, wherein: the catheter lumen has an inner wall that forms a distally extending inward taper at a junction between the catheter proximal section and the catheter distal section; and the support sheath forms a distal tip that is received, or receivable, in the distally extending inward taper to form the common lumen when the support sheath is in the catheter proximal section.

Clause 104. The system of Clause 101, wherein the loading assembly is removably positioned, or removably positionable, within the catheter proximal section with a distal end of the support sheath distal section adjoining a proximal end of the catheter distal section such that the stent can be advanced distally and directly into the catheter distal section from the support sheath distal section.

Clause 105. The system of Clause 101, wherein the core member distal section has a length greater than the combined length of the support sheath distal section and the catheter distal section.

Clause 106. The system of Clause 101, wherein the catheter distal section lumen inner diameter is about equal to the support sheath distal section lumen inner diameter.

Clause 107. The system of Clause 101, wherein the support sheath has a proximal section and the support sheath lumen extends into the support sheath proximal section, and the support sheath lumen has a larger inner diameter in the support sheath proximal section than in the support sheath distal section.

Clause 108. The system of Clause 107, wherein the core member has proximal and distal sections, the core member distal section cross-sectional profile or outer diameter being less than the core member proximal section cross-sectional profile or outer diameter, the core member distal section and the stent being received within the support sheath distal section.

Clause 109. The system of Clause 108, wherein the core member proximal section cross-sectional profile or outer diameter is greater than the catheter distal section lumen inner diameter and the sheath distal section lumen inner diameter.

Clause 110. The system of Clause 107, wherein the support sheath proximal section has an outer diameter that is larger than an outer diameter of the support sheath distal section.

Clause 111. The system of Clause 110, wherein the support sheath distal section outer diameter is larger than the catheter distal section lumen inner diameter.

Clause 112. The system of Clause 101, wherein the catheter proximal section has an outer diameter that is larger than an outer diameter of the catheter distal section.

Clause 113. The system of Clause 101, wherein the catheter proximal section has an outer diameter of at least 0.027 inches, and the catheter distal section has an outer diameter of less than 0.020 inches.

Clause 114. The system of Clause 101, wherein the core member comprises a stent engagement portion for removably securing the stent to the core member.

Clause 115. The system of Clause 114, wherein the stent engagement portion comprises a longitudinal member and a plurality of stiff filaments extending radially from the longitudinal member and engaging an inner luminal surface of the stent.

Clause 116. The system of Clause 115, wherein the stiff filaments comprise bristles.

Clause 117. The system of Clause 114, wherein the stent engagement portion comprises a shaft that extends into a lumen of the stent and a filament wrapped around the stent to secure the stent with respect to the shaft.

Clause 118. The system of Clause 117, wherein the filament is wrapped around only a proximal portion of the stent.

Clause 119. The system of Clause 117, wherein the filament comprises a polypropylene filament.

Clause 120. The system of Clause 117, wherein the filament comprises proximal and distal end portions, the filament proximal end portion being coupled to the core member, the filament distal end portion being unsecured to the stent to permit the filament distal end portion to move freely upon expansion of the stent.

Clause 121. The system of Clause 117, wherein the support sheath distal section inner wall, or the catheter distal section inner wall, holds the wrapped filament in place against an outer surface of the stent when the stent is located in the support sheath distal section or the catheter distal section.

Clause 122. The system of Clause 117, wherein the catheter distal section lumen inner diameter and the sheath distal section lumen inner diameter are diametrically larger than a cross-sectional profile of the filament wrapped around the stent by less than a diameter of the filament.

Clause 123. The system of Clause 114, wherein the stent engagement portion comprises a plurality of protrusions for engaging the stent.

Clause 124. The system of Clause 114, wherein when the stent is coupled to the core member via the stent engagement portion, the core member does not extend distally of the stent.

Clause 125. A method of advancing a stent into a distal section of a catheter having a proximal section, the distal section and an internal lumen wherein the catheter lumen has a smaller diameter in the distal section than in the proximal section, the method comprising: advancing a loading assembly into the proximal section of the catheter, the loading assembly comprising (a) a support sheath having a distal section and a lumen extending through the distal section, and (b) a core assembly comprising a core member and a stent engaged by the core member, the core assembly being slidably received in the support sheath with the stent positioned in the support sheath lumen in the support sheath distal section; positioning a distal tip of the support sheath distal section at or near a proximal end of the catheter distal section and forming an integral delivery lumen from the support sheath distal section lumen and the catheter distal section lumen; and advancing the stent, via the core member, distally from the support sheath distal section into the catheter distal section.

Clause 126. The method of Clause 125, further comprising advancing the catheter distal section into the vasculature of a patient.

Clause 127. The method of Clause 125, further comprising advancing the catheter distal section into the vasculature of a patient before advancing the loading assembly into the proximal section of the catheter.

Clause 128. The method of Clause 125, further comprising advancing at least part of the catheter distal section into the cerebral vasculature of a patient.

Clause 129. The method of Clause 128, further comprising positioning at least part of the catheter proximal section in the non-cerebral vasculature of the patient, and none of the catheter proximal section in the cerebral vasculature.

Clause 130. The method of Clause 125, further comprising advancing at least part of the catheter distal section into the cerebral vasculature of a patient before advancing the loading assembly into the proximal section of the catheter.

Clause 131. The method of Clause 125, wherein the catheter distal section has an outer diameter less than or equal to 0.020 inches.

Clause 132. The method of Clause 131, wherein the catheter proximal section has an outer diameter greater than or equal to 0.027 inches.

Clause 133. The method of Clause 125, further comprising advancing the stent distally through the catheter distal section, out a distal opening of the catheter, and into the vasculature of a patient.

Clause 134. The method of Clause 133, further comprising releasing the stent from the core member into a position across an aneurysm.

Clause 135. The method of Clause 125, wherein positioning the distal tip of the support sheath distal section at or near the proximal end of the catheter distal section comprises inserting the distal tip into a tapering section of an inner wall of the catheter at or near the proximal end of the catheter distal section.

Clause 136. The method of Clause 125, wherein positioning the distal tip of the support sheath distal section at or near the proximal end of the catheter distal section comprises stabilizing the distal tip in a transition portion of the catheter between the catheter proximal section and the catheter distal section.

Clause 137. The method of Clause 125, wherein the entirety of the stent is contained within the support sheath during advancement of the loading assembly into the proximal section of the catheter.

Clause 138. A medical device delivery system, the system comprising: a catheter having proximal and distal sections and a lumen having an inner shoulder between the proximal and distal sections, the catheter lumen having a larger diameter in the proximal section than in the distal section; a support sheath having a distal section and an inner lumen, the support sheath being advanceable within the lumen of the catheter proximal section to contact a distal end portion of the sheath against the catheter inner shoulder to stabilize the sheath within the catheter; and a core member having a distal section, and carrying a medical device via the distal section, the core member distal section cross-sectional profile being less than the sheath distal section lumen inner diameter to allow the medical device and core member distal section to be advanced along the sheath distal section.

Clause 139. The system of Clause 138, wherein the catheter distal section lumen diameter is about equal to the sheath distal section lumen diameter.

Clause 140. The system of Clause 139, wherein the core member has a proximal section and the cross-sectional profile of the core member proximal section is greater than the catheter distal section lumen diameter and the sheath distal section lumen diameter.

Clause 141. The system of Clause 138, wherein the catheter proximal section has an outer diameter of at least 0.030 inches, and the catheter distal section has an outer diameter of less than 0.020 inches.

Clause 142. The system of Clause 141, wherein the catheter proximal section has an outer diameter of at least 0.033 inches, and the catheter distal section has an outer diameter of less than 0.018 inches.

Clause 143. The system of Clause 142, wherein the catheter proximal section has an outer diameter of about 0.035 inches, and the catheter distal section has an outer diameter of about 0.017 inches.

Clause 144. The system of Clause 138, wherein the catheter lumen steps down to a smaller diameter at the inner shoulder between the proximal and distal sections.

Clause 145. The system of Clause 138, wherein the catheter lumen tapers at the inner shoulder between the proximal and distal sections.

Clause 146. The system of Clause 145, wherein the catheter lumen tapers conically in a distal direction.

Clause 147. The system of Clause 145, wherein the sheath distal end portion tapers conically in a distal direction to permit the sheath distal end portion to self-center along a longitudinal axis of the catheter when urged into contact against the catheter inner shoulder.

Clause 148. The system of Clause 138, wherein the sheath has a proximal section and the sheath lumen tapers at an inner shoulder of the sheath between the proximal and distal sections.

Clause 149. The system of Clause 148, wherein the sheath lumen steps down to a smaller diameter at the inner shoulder between the proximal and distal sections.

Clause 150. The system of Clause 148, wherein the sheath proximal section has a larger outer diameter than sheath distal section.

Clause 151. The system of Clause 138, wherein the core member distal section has a length greater than the combined length of the support sheath distal section and the catheter distal section.

Clause 152. The system of Clause 138, wherein the core member has a proximal section and tapers at a core member outer shoulder between the proximal and distal sections.

Clause 153. The system of Clause 138, wherein the core member has a proximal section and steps down to a smaller diameter at an outer shoulder between the proximal and distal sections.

Clause 154. The system of Clause 138, wherein the core member has a proximal section and the cross-sectional profile of the core member proximal section is larger than the catheter distal section lumen diameter and the sheath distal section lumen diameter.

Clause 155. The system of Clause 138, wherein the medical device comprises a stent.

Clause 156. The system of Clause 155, wherein the stent is releasably carried by the core member via a stent engagement portion of the core member.

Clause 157. The system of Clause 156, wherein the stent engagement portion of the core member comprises a longitudinal member and a plurality of stiff filaments extending radially from the longitudinal member and engaging an inner luminal surface of the stent.

Clause 158. The system of Clause 157, wherein the stiff filaments comprise bristles.

Clause 159. The system of Clause 156, wherein the stent engagement portion of the core member comprises a shaft that extends into a lumen of the stent and a filament wrapped around the stent to secure the stent to the shaft.

Clause 160. The system of Clause 159, wherein the filament is wrapped around only a proximal portion of the stent.

Clause 161. The system of Clause 159, wherein the filament comprises a polypropylene filament.

Clause 162. The system of Clause 159, wherein the support sheath distal section inner wall holds the wrapped filament in place against an outer surface of the stent when the stent is located in the support sheath distal section.

Clause 163. The system of Clause 159, wherein the filament comprises proximal and distal end portions, the filament proximal end portion being coupled to the core member, the filament distal end portion being unsecured to the stent to permit the filament distal end portion to move freely upon expansion of the stent.

Clause 164. The system of Clause 159, wherein the catheter distal section lumen diameter and the sheath distal section lumen diameter are diametrically larger than a cross-sectional profile of the filament wrapped around the stent by less than a diameter of the filament.

Clause 165. The system of Clause 156, wherein the stent engagement portion of the core member comprises a plurality of protrusions for engaging the stent.

Clause 166. The system of Clause 156, wherein when the stent is coupled to the core member via the stent engagement portion, the core member does not extend distally of the stent.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 2A is a side, cross-sectional view of the delivery system of FIGS. 1A-B during sequential advancement of components of the system in order to deliver a medical device, according to some embodiments.

FIG. 2B is a side, cross-sectional view of the delivery system of FIGS. 1A-B during sequential advancement of components of the system in order to deliver a medical device, according to some embodiments.

FIG. 2C is a side, cross-sectional view of the delivery system of FIGS. 1A-B during sequential advancement of components of the system in order to deliver a medical device, according to some embodiments.

FIG. 2D is a side, cross-sectional view of the delivery system of FIGS. 1A-B during sequential advancement of components of the system in order to deliver a medical device, according to some embodiments.

FIG. 2E is a side, cross-sectional view of the delivery system of FIGS. 1A-B during sequential advancement of components of the system in order to deliver a medical device, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

FIG. 1A-2E depict embodiments of components of a medical device delivery system 100 which may be used to deliver and/or deploy a medical device into a hollow anatomical structure such as a blood vessel. The type of medical device that can be delivered using the system 100 can vary widely, as can the applications in which the system 100 can be used. For example, the system 100 can deliver medical devices, such as but not limited to stents, occluders or vascular plugs, coils, foam components, braided spheres, and/or other flow diverting, occlusive, and/or intrasaccular devices for treating aneurysms. Further, the system 100 can be configured such that the medical device is releasably or non-releasably attached thereto. Moreover, any coupling between the medical device and the system 100 can be done using mechanical, electrolytic, chemical, or other means that can permit the system 100 to control distal advancement, proximally retracting or receive the medical device, and/or release the medical device into the vasculature.

In the illustrated embodiments, the medical device comprises a stent, 102. The stent 102 can comprise a proximal end 104 and a distal end 106. The stent 102 can comprise a braided stent or other form of stent such as a laser-cut stent, roll-up stent, etc. The stent 102 can optionally be configured to act as a "flow diverter" device for treatment of aneurysms, such as those found in blood vessels including arteries in the brain or within the cranium, or in other locations in the body such as peripheral arteries. The stent 102 can optionally be similar to any of the versions or sizes of the PIPELINE™ Embolization Device marketed by Covidien of Mansfield, Mass. USA. The stent 102 can further alternatively comprise any suitable tubular medical device and/or other features, as described herein.

Figure 1A:
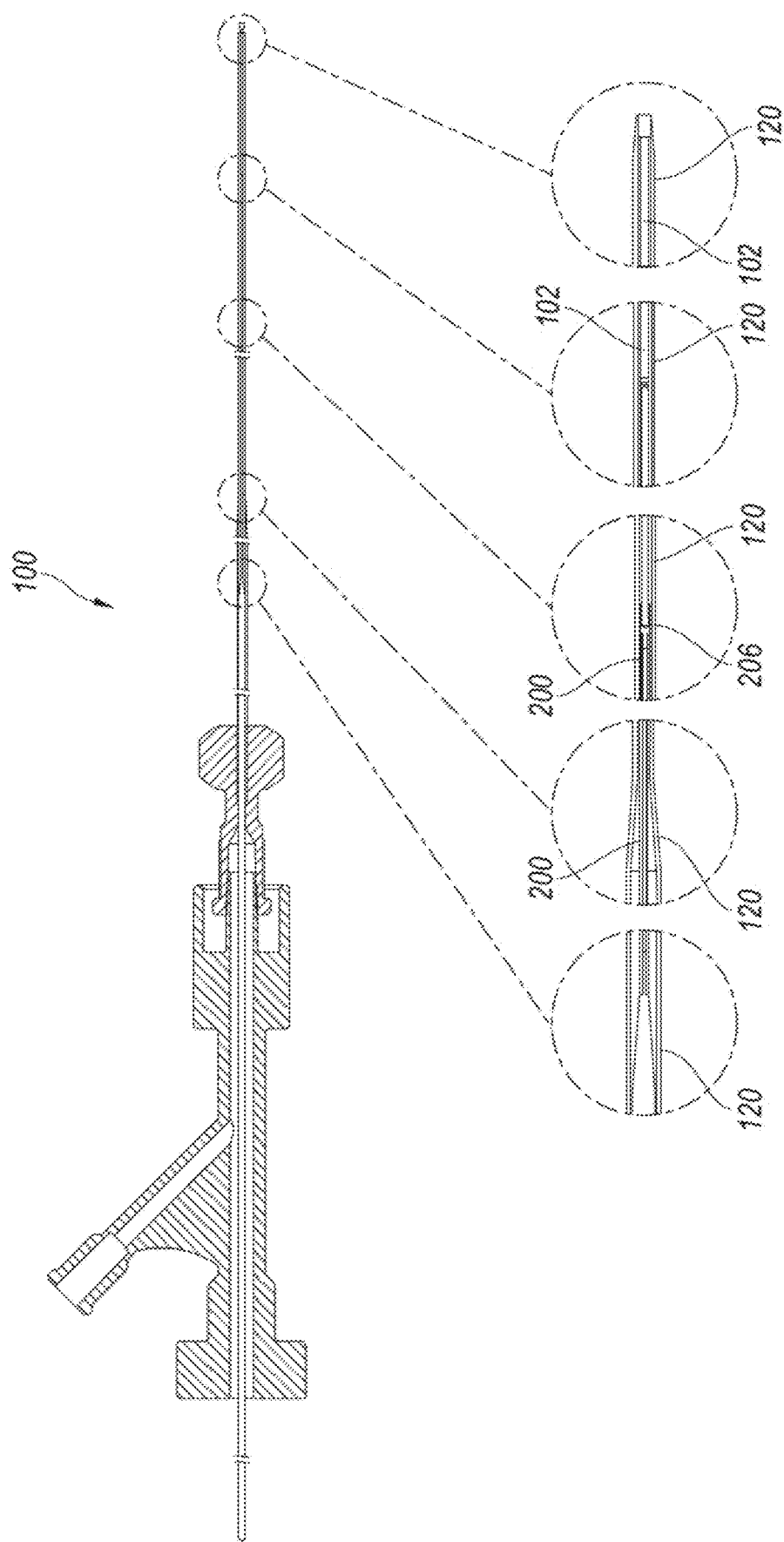
FIG. 1A is a side, cross-sectional view of a medical device loaded into a core assembly of a medical device delivery system, according to some embodiments.

FIG. 1A illustrates proximal components of the system 100 and a core assembly 110 that is coupled to the proximal components. The proximal components can include connector devices and/or actuation components that permit manipulation of components of the system 100. For example, the proximal components can include luers, connectors, flush ports, handles, and other actuation equipment that can manipulate the longitudinal or rotational position of components of the system 100 within the vasculature of a patient.

Figure 1B:
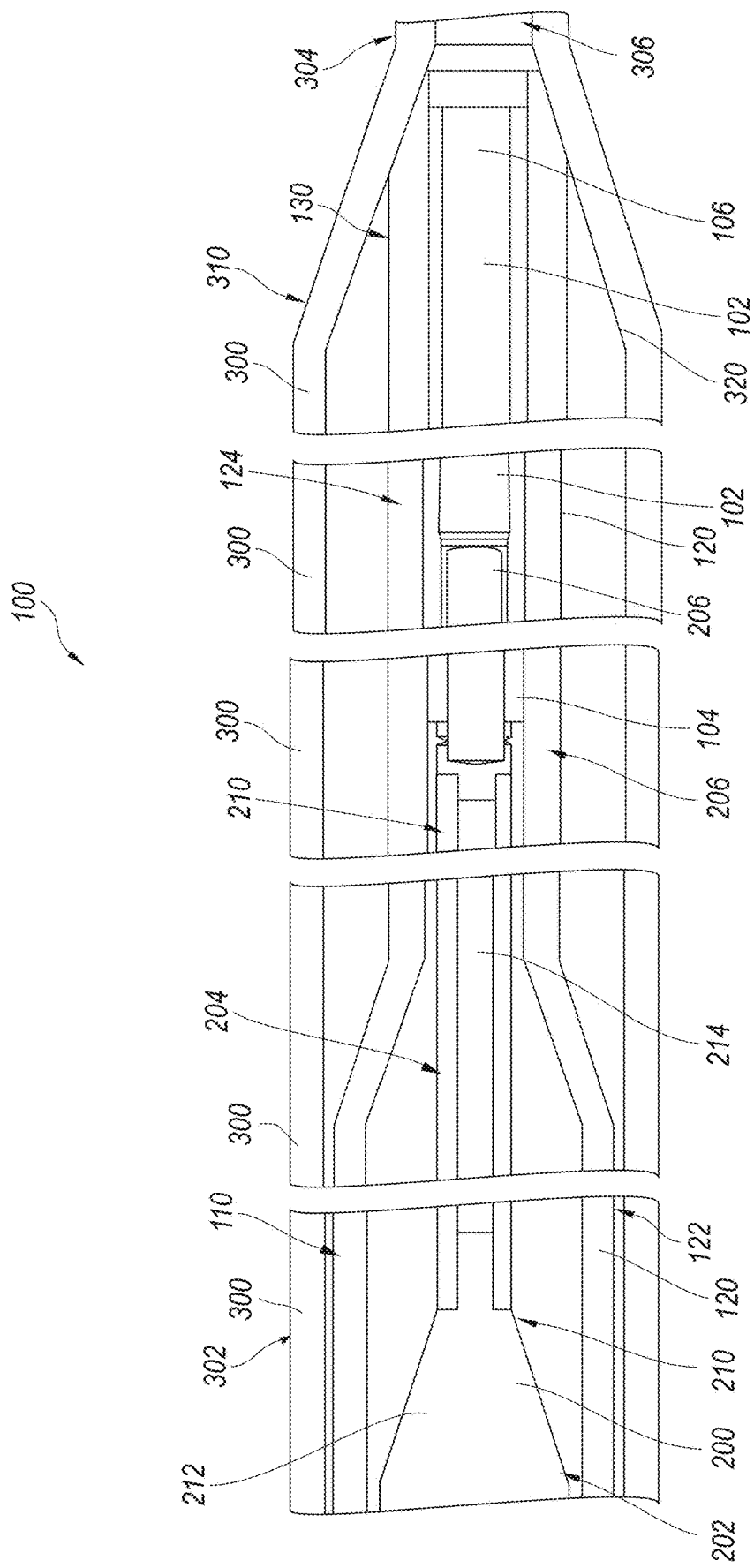
FIG. 1B is a side, cross-sectional view of the core assembly of FIG. 1A loaded into a microcatheter of the medical device delivery system, according to some embodiments.

The system 100 can be configured such that the core assembly 110 comprises an support sheath 120 and a core member 200. The core member 200 can be coupled to, support, or carry a medical device, such as a stent 102. The stent 102 can comprise a proximal end 104 and a distal end 106. As shown in FIGS. 1A and 1B, the proximal end 104 of the stent 102 can be coupled to the core member 200.

In some embodiments, the stent 102 can be loaded into the support sheath 120 as a kit, as shown FIG. 1A. For example, in a preloaded or first position, a proximal portion 202 of the core member 200 can be positioned within a proximal portion 122 of the sheath 120, and a distal portion 204 of the core member 200 can be positioned within a distal portion 124 of the sheath 120. Thus, the stent 102 can be positioned within a lumen of the distal portion 124 of the sheath 120, readied for advancement and delivery into a patient's vasculature. This assembly of the sheath 120, the core member 200, and the stent 102 (i.e., the core assembly 110) can be so assembled and provided to a clinician as a loading assembly, in this assembled configuration, as shown in FIG. 1A (FIG. 2A illustrates the core assembly 110 independently of other components of the system 100). Advantageously then, when manufactured, the core assembly 110 can be assembled with the stent 102 preloaded into the support sheath 120 and coupled to the core member 200.

As illustrated in FIG. 1B, the proximal portion 202 of the core member 200 can comprise an outer diameter that fits closely within an inner diameter of the lumen of the proximal portion 122 of the sheath 120. For example, the outer cross-sectional profile of the proximal portion 202 of the core member 200 can have a diameter of less than about 0.040 inches, between about 0.020 inches and about 0.040 inches, between about 0.025 inches and about 0.038 inches, or between about 0.030 inches and about 0.035 inches. As such, the core member 200 can provide excellent column strength along a majority of its length. Further, the distal portion 204 of the core member 200 can have a lower cross-sectional profile than the proximal portion 202. Nevertheless, any length of the distal portion 204 extending within the proximal portion 122 of the sheath 120 can provide sufficient column strength to allow a pushing force exerted on the core member 200 to be transferred effectively to the stent 102 coupled to the core member 200. For example, the outer cross-sectional profile of the distal portion 204 of the core member 200 can have a diameter of less than about 0.020 inches, between about 0.005 inches and about 0.020 inches, between about 0.010 inches and about 0.018 inches, or between about 0.012 inches and about 0.015 inches.

With regard to the coupling between the core member 200 and the medical device (e.g., the stent 102), various medical device engagement mechanisms can be employed. As shown in FIGS. 1A and 1B, the core member 200 can comprise a stent engagement portion 206 that is coupled to a distal end portion 210 of the core member 200. Some embodiments of medical device engagement mechanisms are illustrated in FIGS. 4-21 and discussed further below.

Additionally, the core member 200 can optionally comprise separate components forming the proximal portion 202 and the distal portion 204. For example, the proximal portion 202 can comprise a longitudinal member, such as a core wire 212. The core wire 212 can be configured as a solid elongate wire formed as a single piece of material. The distal portion 204 can comprise a tubular member 214 that can be coupled to a distal end of the core wire 212. For example, in the embodiment illustrated in FIG. 1B, the core wire 212 can be coupled to the tubular member 214 by inserting a distalmost portion of the core wire 212 into a lumen of the tubular member 214, as shown in FIG. 1B. Further, the stent engagement portion 206 can also be coupled to the tubular member 214 by inserting a proximalmost portion of the stent engagement portion 206 into the lumen of the tubular member 214.

The sheath 120 can be configured such that the proximal portion 122 of the sheath 120 has a larger outer cross-sectional profile than the distal portion 124 thereof. For example, the outer cross-sectional profile of the proximal portion 122 can have a diameter of between about 0.020 inches and about 0.050 inches, between about 0.025 inches and about 0.045 inches, or between about 0.030 inches and about 0.040 inches. Further, the outer cross-sectional profile of the distal portion 124 can have a diameter of between about 0.010 inches and about 0.030 inches, between about 0.015 inches and about 0.028 inches, or between about 0.020 inches and about 0.025 inches.

Additionally, in some embodiments, the lumen of the sheath 120 can be configured such that in the proximal portion 122, the lumen has a larger inner diameter than the lumen in the distal portion 124. For example, the inner diameter of the lumen in the proximal portion 122 can be between about 0.015 inches and about 0.045 inches, between about 0.020 inches and about 0.040 inches, or between about 0.025 inches and about 0.035 inches. Further, the inner diameter of the lumen in the distal portion 124 can be between about 0.005 inches and about 0.025 inches, between about 0.010 inches and about 0.023 inches, or between about 0.015 inches and about 0.020 inches.

Referring still to FIG. 1B, the medical device delivery system 100 can comprise an elongate tube or microcatheter 300 which slidably receives the core assembly 110. The depicted microcatheter 300 has a proximal portion 302 and a distal portion 304 which can be positioned at a treatment site within a patient. The microcatheter 300 also comprises an internal lumen extending from the proximal portion 302 to the distal portion 304. At the distal portion 304, the microcatheter 300 has a distal opening 306 through which the core assembly 110 may be advanced beyond the distal portion 304 in order to expand or deploy the stent 102 within the blood vessel. The proximal portion 302 may include a catheter hub (not shown). The microcatheter 300 can define a generally longitudinal axis A-A extending between the proximal portion 302 and the distal portion 304. When the delivery system 100 is in use, the longitudinal axis need not be straight along some or any of its length.

In some embodiments, the microcatheter 300 can have a variable or stepped diameter outer profile that allows the distal portion 304 to be advanced into blood vessels having sizes that are less 5 Fr or less, such as between about 2 Fr to about 4 Fr, and in some embodiments, less than 2 Fr. For example, some embodiments of the microcatheter 300 can comprise a transition section 310 were at the lumen of the microcatheter 300 decreases from a first diameter in the proximal portion 302 to a second diameter in the distal portion 304. The transition section 310 can comprise a shoulder 320 that extends radially inwardly from the proximal portion 302 in order to restrict advancement of the core assembly 110 within the lumen of the microcatheter 300.

For example, in accordance with some embodiments, the distal portion 124 of the sheath 120 can comprise a distal end portion 130 that can contact the shoulder 320 of the microcatheter 300. The contact between the distal end portion 130 and the shoulder 320 can restrict further distal advancement of the sheath 120 within the lumen of the microcatheter 300 as shown FIGS. 1B and 2B. After the distal end portion 130 is in abutting contact with the shoulder 320, the core member 200 can be moved distally within the sheath 120, thereby advancing the stent 102 out from the lumen of the sheath 120 and distally beyond the distal portion 122 of the sheath 120. As such, the sheath 120 can facilitate advancement of the stent 102 within the vasculature to a location after which the vasculature narrows. The stent 120 is maintained in a collapsed state after being advanced into the microcatheter distal portion 304. With continued advancement, the stent 102 can eventually be released from the microcatheter 300 by exiting the distal opening 306 of the microcatheter 300, as shown in FIGS. 2C-2E.

In some embodiments, distal end portion 130 can taper in the distal direction. For example, the distal end portion 130 can comprise a conical shape. Accordingly, in some embodiments, the shoulder 320 of the microcatheter 300 can also taper in the distal direction, and optionally, the shoulder 320 can comprise a conical shape against which the distal end portion 130 of the sheath 120 can be mated, as shown in FIG. 1B. This mating or abutment of the sheath distal end portion 130 against the shoulder 320 of the microcatheter 300 can serve to facilitate self-centering of the sheath 120 within the microcatheter lumen. In particular, the lumen of the sheath 120 can be axially aligned with the lumen of the microcatheter 300 by using a self-centering mechanism, such as that noted herein.

In some embodiments, the sheath distal end portion 130 can be relatively rigid, e.g., more rigid than the shaft of the introducer sheath in the region just proximal of the distal end portion 130. This can be accomplished by employing a more rigid material and/or heavier construction than the proximally adjacent shaft. Examples of materials for the distal end portion 130 include metals, ceramics, sapphire, glass, and rigid polymers. A relatively rigid distal end portion 130 will tend to preserve its shape and therefore facilitate more effective "plug-in" of the distal end portion 130 into the shoulder 320 of the microcatheter.

In some embodiments, the microcatheter 300 can have an inner diameter of about 0.030 inches or less, about 0.025 inches or less, about 0.020 inches or less, or about 0.019 inches or less, and/or an outer diameter of about 0.035 inches or less, about 0.025 inches or less, or about 0.020 inches or less along the distal portion 304. For example, some embodiments can be configured such that the microcatheter outer diameter along the distal portion 304 is 0.018 inches or less, such as 0.017 inches. Further, the microcatheter 300 can have an outer diameter of 0.025 inches or more along the proximal portion 302. For example, the microcatheter outer diameter along the proximal portion 302 can be at least 0.030 inches, and in some embodiments, about 0.35 inches.

Information regarding additional embodiments of the microcatheter 300, and additional details and components that can optionally be used or implemented in the embodiments of the microcatheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

As noted above, the distal portion 204 of the core member 200 can be distally advanced within the microcatheter 300 until the stent 102 can be unsheathed and subsequently released into position in the lumen of the vessel, e.g., across and/or spanning a neck of an aneurysm formed in the wall of the vessel, or the stent 102 can be retracted and withdrawn back into the microcatheter 300 (by virtue of the engagement between the stent engagement portion 206 and the proximal end 104 of the stent 102), if needed.

Referring again to FIG. 1A, in some embodiments, the core assembly 110 (and optionally together with the stent 102 or medical device carried thereby) can be packaged in, or pre-loaded in an support sheath 120 to thereby form a pre-load assembly 100. Such a pre-load assembly 100 and support sheath 120 can facilitate rapid transfer of the core assembly 110 and stent 102 into the microcatheter 300 via the hub 122 and/or proximal portion 302. This can enable, for example, the microcatheter 300 to be selected independently of the core assembly 110 and stent 102. The core assembly 110 and stent 102 can be packaged in a pre-loaded condition in the support sheath 120 (e.g., with the resulting pre-load assembly in a coiled configuration), and the support sheath connected to the proximal end of the microcatheter 300 to enable delivery of the stent 102 via the microcatheter 300. The support sheath can have an inside diameter that is approximately equal to the inside diameter of the microcatheter 300, and a tapered distal tip (not shown) to facilitate connection with the proximal end of the microcatheter 300.

FIGS. 2A-2E depict some embodiments and methods of use of the medical device delivery system 100. First, the microcatheter 300 can be inserted into the patient's vasculature via a percutaneous access technique or other suitable method of access. The distal portion 304 of the microcatheter 300 is then advanced to a treatment site or location in the blood vessel, using for example any appropriate access routes. The blood vessel may comprise a vein or artery, such as an artery in a brain or within a cranium of the patient. A guide catheter (not shown) can be used instead of or in addition to the microcatheter 300; for example, the guide catheter can first be placed in the vasculature so that it extends part or all of the way to the treatment site and a microcatheter or other catheter then inserted through the guide catheter to the treatment site.

The treatment location may be near the aneurysm formed in a wall of the blood vessel, and advancing the microcatheter 300 to the treatment location may include advancing the distal portion 304 and/or distal opening 306 to a location that is distal of the aneurysm. Such advancement of the microcatheter 300 may include advancing the distal portion 304 and/or distal opening 306 distally across the ostium or neck of the aneurysm, to the location in the vessel distal of the aneurysm.

Once the microcatheter 300 has been inserted, it may extend proximally from the distal portion 304 and/or distal opening 306 at the treatment location, through the vascular access site, to the proximal portion 302 and/or a hub of the microcatheter 300, which are preferably situated outside the patient's body.

After the microcatheter 300 has been placed, the core assembly 110 (with the stent 102 carried thereby, as shown in FIG. 2A) can be inserted, distal end first, into the lumen of the microcatheter 300 via the hub 122 and/or proximal portion 302, as shown in FIG. 2B. The distal end portion 130 of the support sheath 120 can be inserted into the proximal end of the microcatheter 300 until the distal end portion contacts the shoulder 320 of the transition section 310 of the microcatheter 300. Thereafter, the core assembly 110 is advanced distally through the support sheath 120 until the distal portion 204 of the core member 200 and the stent 102 are positioned within the distal portion 304 of the microcatheter 300, as shown FIG. 2C.

With the microcatheter distal opening 306 in position at the target site, the core member 200 can be further advanced within the sheath 120 and the microcatheter 300 until the stent 102 exits the distal opening 306 of the microcatheter 300. The stent engagement portion 206 can securely engage a portion of the stent 102 until the engaged portion or the entirety of the stent 102 is advanced distally beyond the distal opening 306. At any point prior to release of the stent 102 from the engagement portion 206, the stent 102 can be proximally withdrawn into the lumen of the microcatheter 300. This proximal withdrawal of the stent 102 can be performed in instances where the distal opening 306 is not in proper position to optimize the release location of the stent 102. Once the stent 102 is determined to be releasable in the proper location at the target area and the stent 102 is released, the core member 200 can be retracted from the distal portion 304 of the microcatheter 300, into the sheath 120, and optionally, out through the sheath 120. However, the core member 200 can be withdrawn into the sheath 120, and the core assembly 110 can be removed as a unit from the microcatheter 300.

Accordingly, in accordance with some embodiments of methods disclosed herein, when operating the delivery system 100, a clinician can check the initial partial expansion of the stent 102 (e.g., as shown in FIG. 2D) and, if the initial placement within the blood vessel is unsatisfactory or if the initial expansion of the stent 102 is unsatisfactory, the clinician can recapture, collapse, withdraw, or resheath the stent 102 into the microcatheter 300 by exerting a proximal force on the microcatheter 300 while the stent engagement mechanism 206 is coupled to the stent 102. After resheathing, the clinician can attempt to deploy the stent again. Resheathing can also be performed, and the delivery system 100 and stent 102 removed from the patient entirely, if for example, the delivery and/or expansion of the stent 102 damages or reveals a defect in, or improper sizing of, the stent 102 or delivery system 100. After an initial partial expansion of the stent 102, the depicted core assembly 110 can optionally be entirely removed with the stent 102 from the microcatheter 300 without need to remove the microcatheter 300 from the blood vessel. In this manner, access to the treatment site in the blood vessel can be maintained via the microcatheter 300 and, if desired, additional attempts to deliver the stent 102 can be made through the microcatheter 300.

If the initial expansion of the stent 102 in the vessel is satisfactory, full deployment and expansion can be completed to result in the state depicted in FIG. 2E. The proximal end 104 of the stent 102 may be released from the microcatheter 300 by holding the core member 200 stationary and withdrawing the microcatheter proximally relative to the core member 200 and the stent 102 until the distal opening 306 is proximal of the proximal end 104 of the stent 102. No longer constrained by the microcatheter 300, the proximal end 104 of the stent 102 can now expand into contact with the wall of the vessel. (Note that until this point, according to an aspect of some embodiments, the partially expanded stent 102 had been fully resheathable.) The fully deployed stent 102 extends across the neck of the aneurysm, and can optionally perform a therapeutic flow-diverting function with respect to the aneurysm.

Following full expansion of the stent 102, the core assembly 110 can be drawn back into the microcatheter 300. Both the microcatheter 300 and core assembly 110 can be withdrawn from the patient, either simultaneously or sequentially. However, when the stent has been successfully released, the core assembly 110 can also be entirely removed from the microcatheter 300, with the microcatheter 300 remaining in place, and a second core assembly can be inserted into the microcatheter lumen. The second core assembly can be configured to deliver a second stent to the treatment site in order to perform, e.g., a telescoping procedure.

In the present disclosure, numerous references are made to moving the microcatheter 300 axially over the core assembly 110, and moving the core assembly 110 axially within the microcatheter 300. Except where specifically noted to the contrary, all such references to one form of this relative movement should be understood to include the other as an alternative.

Medical Device Engagement Mechanisms

As discussed above, the medical device delivery system 100 can comprise a medical device engagement mechanism in order to be coupled with the medical device and enable the system 100 to exert a distal pushing force, and in some embodiments, a proximal pulling force on the medical device during operation of the system 100.

Figure 3A:
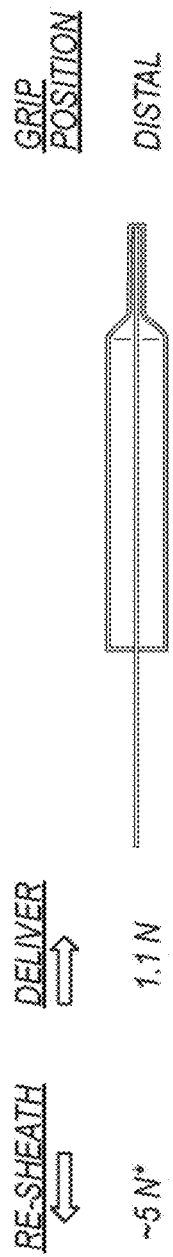
FIG. 3A illustrates an engagement mode by which a medical device engagement mechanism can engage a stent, for example, according to some embodiments.
Figure 3B:
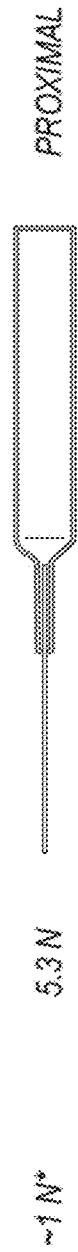
FIG. 3B illustrates an engagement mode by which a medical device engagement mechanism can engage a stent, for example, according to some embodiments.
Figure 3C:
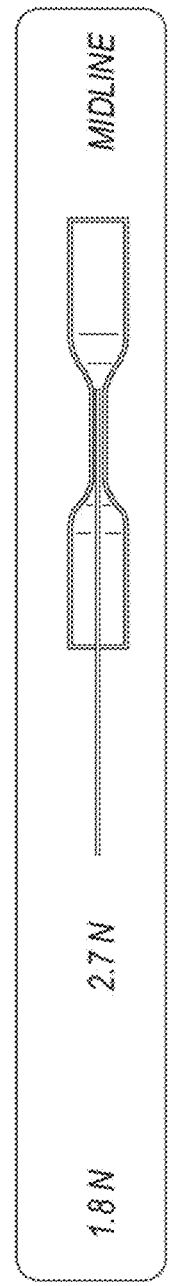
FIG. 3C illustrates an engagement mode by which a medical device engagement mechanism can engage a stent, for example, according to some embodiments.
Figure 3D:
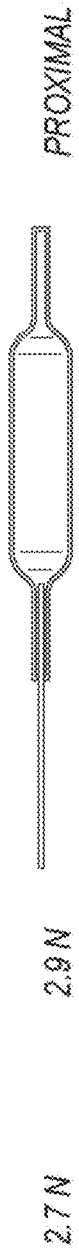
FIG. 3D illustrates an engagement mode by which a medical device engagement mechanism can engage a stent, for example, according to some embodiments.

FIGS. 3A-3D illustrate grip positions of an engagement mechanism when coupled to a medical device. In the embodiment of FIG. 3A, restraining a medical device, such as the stent, from its distal end yields the lowest delivery forces as the stent contracts when pulled, but may leave the tip of the core member 200 exposed distal to the deployed stent. Further, such a configuration may also result in higher re-sheathing forces. FIGS. 3B and 3D illustrate proximal end engagement of a stent, which yields the highest delivery forces due to stent expansion when the stent is being pushed through the sheath and microcatheter lumens. FIG. 3C demonstrates stent restraint from a midline or middle portion which yields moderate forces during distal and proximal refraction of the stent within microcatheter lumen, because half of the stent is contracting and half is expanding, and no core member tip is exposed distal to the stent after release. As noted in FIGS. 3A-3D, the midline grip position of FIG.

3C has been determined (through testing) to require the lowest combined forces to resheath and deliver a stent when compared to the other grip positions discussed herein.

Additionally, it has been determined that very small diameter core members may not be sufficiently strong to transmit high distal forces. For example, a wire having a diameter of 0.009 inches only has a maximum push force of 2.1 N. however, a wire having a diameter of 0.012 inches has a maximum push force of 2.8 N. Further, a wire having a diameter of 0.021 inches can withstand a maximum push force of 4.5 N. Finally, a wire having a diameter of 0.032 inches can withstand a maximum push force of 5.5 N.

Some embodiments of medical device engagement mechanisms are illustrated in FIGS. 4-21 and discussed further below.

Figure 4:
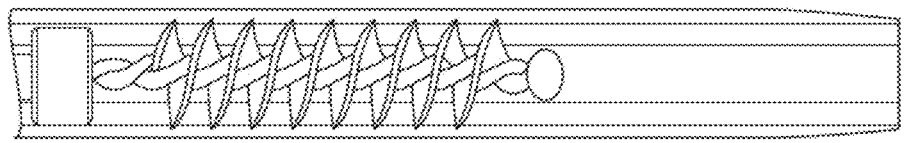
FIG. 4 illustrates a medical device engagement mechanism, according to some embodiments.
Figure 5:
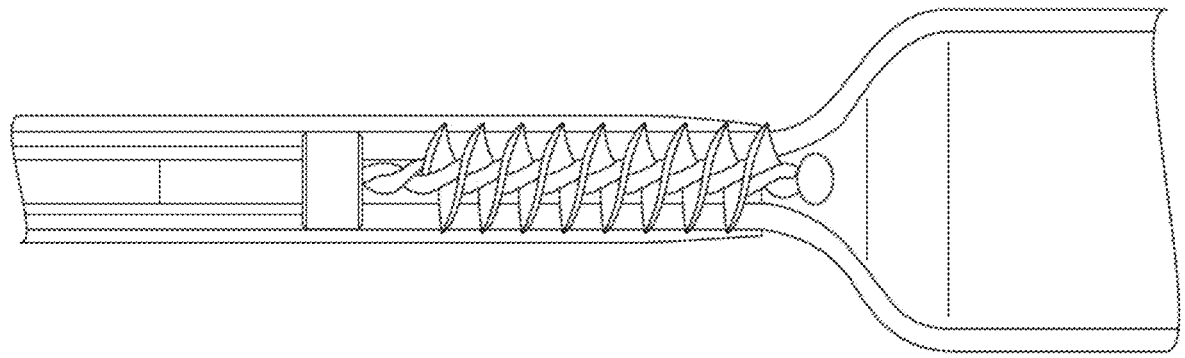
FIG. 5 illustrates a medical device engagement mechanism, according to some embodiments.

FIGS. 4-5 illustrate a medical device engagement mechanism that can comprise a miniature cytology-type brush to engage an inner surface of a stent, such as a braid structure, prior to compacting into the support sheath during loading of the stent into the sheath. The rush can comprise filaments or bristles that can be stiff and/or soft. For example, soft flexible brush bristles can be slightly larger than the inner diameter of the sheath and the inner diameter of the microcatheter. The distal tip of the twisted brush wires can be joined and balled using a laser welder.

Figure 6:
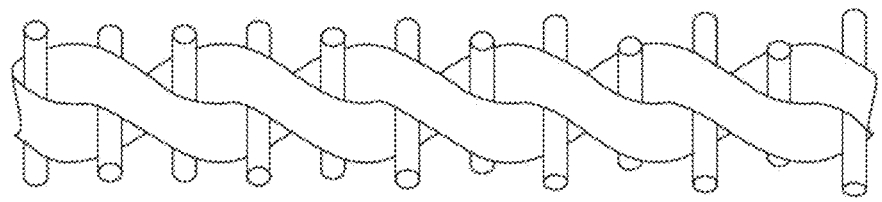
FIG. 6 illustrates another medical device engagement mechanism, according to some embodiments.
Figure 7:
FIG. 7 illustrates another medical device engagement mechanism, according to some embodiments.
Figure 8:
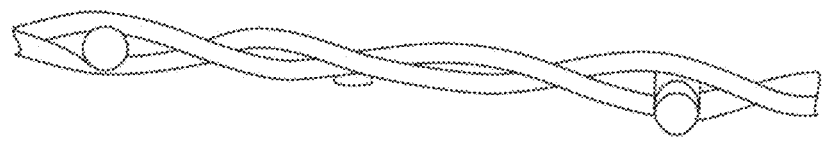
FIG. 8 illustrates another medical device engagement mechanism, according to some embodiments.

FIGS. 6-8 illustrated another medical device engagement mechanism, similar to the embodiment shown in FIGS. 4-5. In this embodiment, the engagement mechanism can comprise a pair of helically wound wires and bristles that are positioned in openings between the helically wound wires. For example, the engagement mechanism in FIGS. 6-8 can comprise ten 0.004 inch individual bristles or 20 pins that fit into braid openings. This can provide a low bristle density while still enabling the engagement mechanism to adequately engage the inner surface of the stent. Through testing, it has been determined that such mechanisms can permit distal or proximal forces up to 2.1 N to be exerted on the stent.

Figure 9:
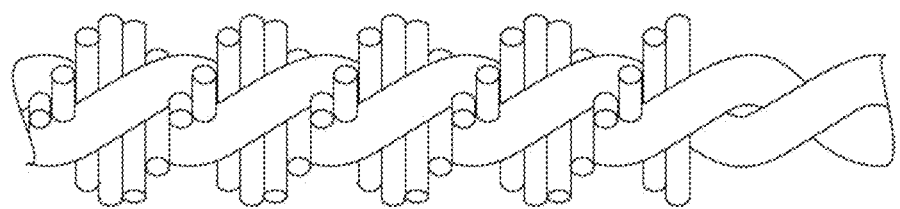
FIG. 9 illustrates yet another medical device engagement mechanism, according to some embodiments.
Figure 10:
FIG. 10 illustrates yet another medical device engagement mechanism, according to some embodiments.
Figure 11:
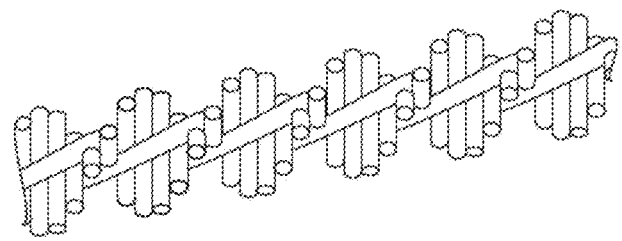
FIG. 11 illustrates yet another medical device engagement mechanism, according to some embodiments.
Figure 12:
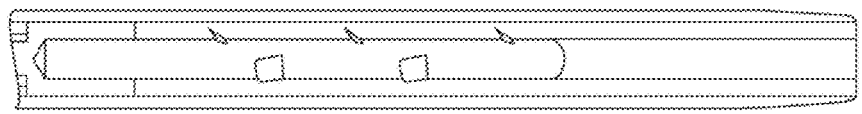
FIG. 12 illustrates yet another medical device engagement mechanism, according to some embodiments.
Figure 13:
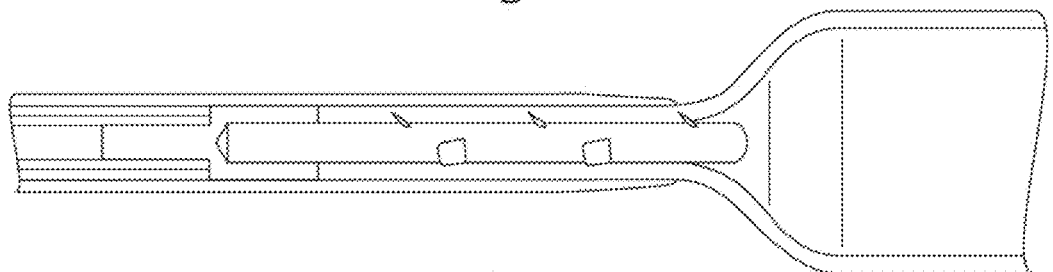
FIG. 13 illustrates yet another medical device engagement mechanism, according to some embodiments.
Figure 14:
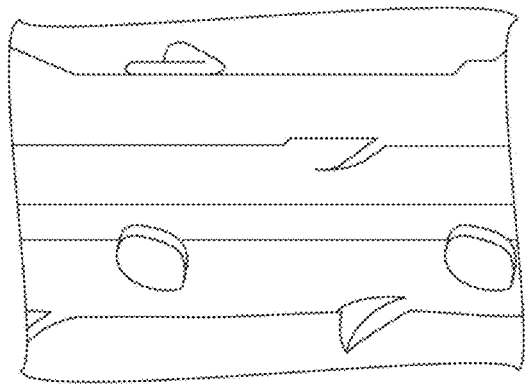
FIG. 14 illustrates yet another medical device engagement mechanism, according to some embodiments.
Figure 15:
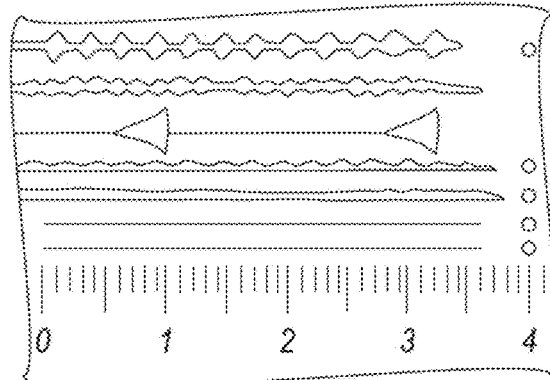
FIG. 15 illustrates yet another medical device engagement mechanism, according to some embodiments.

FIGS. 9-11 illustrate yet another medical device engagement mechanism, according to some embodiments. In this embodiment, similar to that shown in FIGS. 6-8, the engagement mechanism can comprise a pair of helically wound wires and bristles that are positioned in openings between helically wound wires. However, the engagement mechanism of FIGS. 9-11 can comprise individual 0.001 inch diameter bristles to fit into braid openings. Further, it has been determined that too many bristles they tend to permit some slippage of the engagement mechanism relative to the stent inner surface.

FIGS. 12-15 illustrate yet another medical device engagement mechanism, according to some embodiments. The illustrated engagement mechanism can comprise a short length of non-absorbable barbed suture, such as Covidien Polybutester V-Loc PBT suture. This suture can be attached to the distal end of the core member. The suture can be placed into or otherwise coupled to the stent and compacted into the support sheath where the barbs allow the stent to be retracted by the suture.

Figure 16:
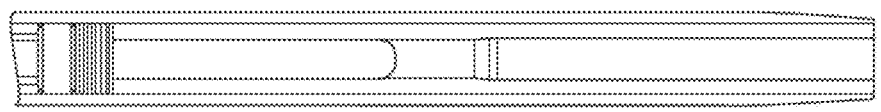
FIG. 16 illustrates yet another medical device engagement mechanism, according to some embodiments.
Figure 17:
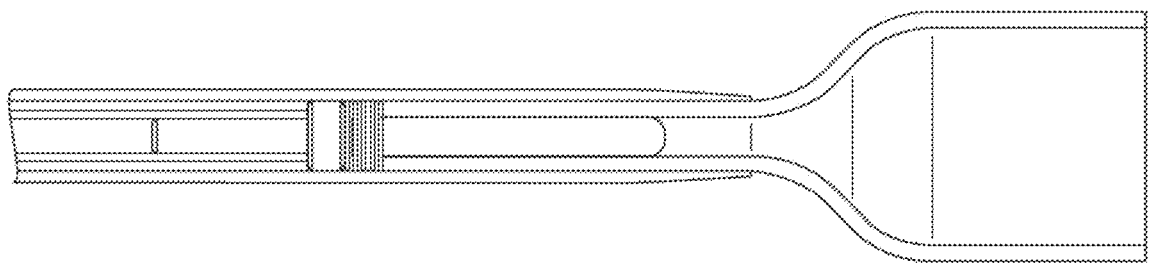
FIG. 17 illustrates yet another medical device engagement mechanism, according to some embodiments.

FIGS. 16-17 illustrate yet another medical device engagement mechanism, according to some embodiments. In this embodiment, a suture (e.g., a 0.001 inch suture) is attached to a pin of the engagement mechanism. The stent is slid onto the pin and wrapped (whipped) to the pin using the suture. The tag were distal end of the suture is left free (unattached to the engagement mechanism as the wrapped assembly is loaded into the support sheath. The positioning of the suture within the microcatheter lumen in the distal portion of the microcatheter (which provides a close tolerance between the outer profile of the stent and engagement mechanism and the inner profile of the microcatheter, which prevents the suture from unwrapping. When the stent is pushed from the delivery microcatheter and the unattached free end of the suture is exposed, the suture is free to un-wrap and allow the stent to expand.

Figure 18:
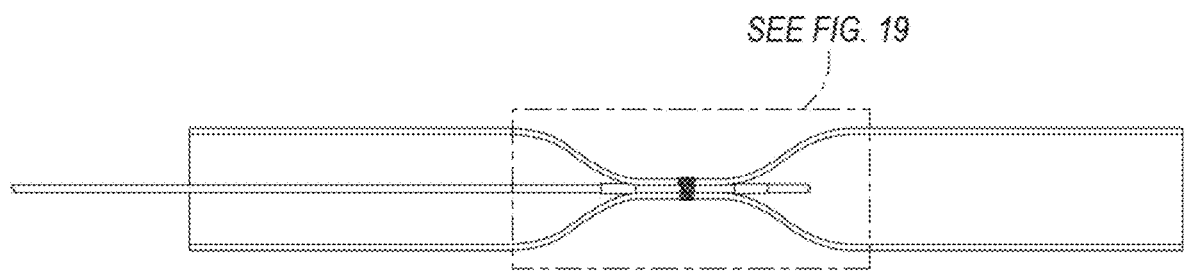
FIG. 18 illustrates yet another medical device engagement mechanism, according to some embodiments.
Figure 19:
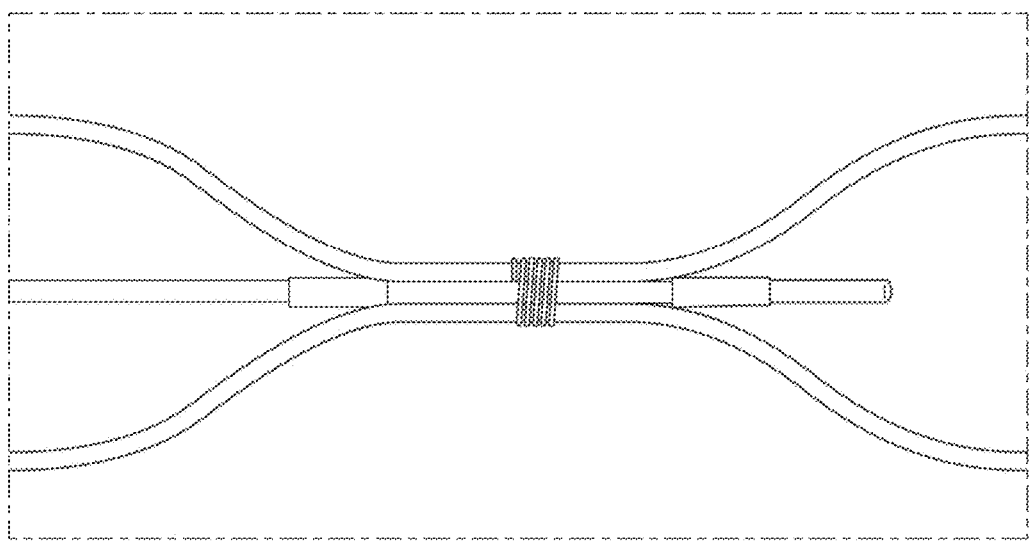
FIG. 19 illustrates yet another medical device engagement mechanism, according to some embodiments.

FIGS. 18-19 illustrate yet another medical device engagement mechanism, according to some embodiments. This embodiment of the engagement mechanism operates in the same fashion as that shown in FIG. 16-17. However, the suture is attached to a midsection of the stent instead of a proximal section of the stent, as in FIG. 16-17. This is so to optimize the pushability and retractability of the system using a midpoint suture engagement.

Figure 20:
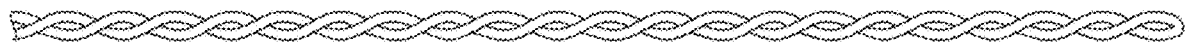
FIG. 20 illustrates yet another medical device engagement mechanism, according to some embodiments.
Figure 21:
FIG. 21 illustrates yet another medical device engagement mechanism, according to some embodiments.

FIGS. 20-21 illustrate yet other medical device engagement mechanisms, according to some embodiments. These mechanisms illustrate that in some embodiments, other materials can be braided into the wires and extend along a longitudinal length of the helix, as shown in FIG. 20. Further, FIG. 21 illustrates that the engagement mechanism can comprise coiled wires can have a variable helix spacing or sizing along a portion of the length of the engagement mechanism.

Information regarding additional embodiments of the medical device delivery system 100, and additional details, components and methods that can optionally be used or implemented in or with the embodiments of the delivery system 100 described herein, can be found in U.S. patent application Ser. No. 13/664,547, filed on Oct. 31, 2012, titled METHODS AND APPARATUS FOR LUMINAL STENTING, the entirety of which is hereby incorporated by reference herein and made a part of this specification. The delivery system 100 and methods disclosed herein can optionally be similar to any of the delivery systems or methods disclosed in the above-incorporated application, except as further described herein.

The apparatus and methods discussed herein are not limited to the deployment and use of a medical device or stent within the vascular system but may include any number of further treatment applications. Other treatment sites may include areas or regions of the body including any hollow anatomical structures.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

The invention claimed is:
1. An assembly for a medical device delivery system, the assembly comprising:

an introducer sheath having a sheath proximal section, a sheath distal section, a sheath lumen, and an inner shoulder between the sheath proximal and distal sections, the sheath lumen having a first diameter in the sheath proximal section and a second diameter less than the first diameter in the sheath distal section, wherein the sheath proximal section has a length of at least 100 cm and the sheath distal section has a length of at least 30 cm, the sheath distal section having a substantially constant lumen diameter;

a core member having a core member proximal section, a core member distal section, an outer shoulder between the core member proximal and distal sections, and a stent engagement portion at the core member distal section for coupling a stent thereto; and a catheter having a catheter proximal section, a catheter distal section, a catheter lumen, and a transition section between the catheter proximal and distal sections, wherein the catheter lumen distally tapers to a smaller diameter at the transition section, wherein the introducer sheath is configured to be advanced within the catheter lumen such that a distal end of the introducer sheath contacts the transition section of the catheter, wherein the distal end of the introducer sheath tapers conically in a distal direction and is configured to self-center along a longitudinal axis of the catheter when urged into contact with the transition section, and wherein the sheath lumen in the sheath distal section and the catheter lumen in the catheter distal section together form a common lumen having a substantially constant diameter;

wherein the core member distal section is configured to be positioned within the sheath lumen along the sheath distal section and proximal to the distal end of the introducer sheath in a first position, the core member distal section having a length greater than a combined length of the sheath distal section and the catheter distal section, and wherein a cross-sectional profile of the core member distal section is less than the second diameter of the sheath lumen to allow the core member distal section and the stent to be advanced within the sheath distal section until the outer shoulder converges toward the inner shoulder such that the core member distal section extends beyond the distal end of the introducer sheath and beyond a distal end of the catheter in a second position in which the distal end of the introducer sheath abuts the transition section of the catheter.

2. The assembly of claim 1, wherein the distal end of the introducer sheath is positioned adjacent to a distal end of the core member in the first position.

3. The assembly of claim 1, wherein the inner shoulder is spaced apart from the outer shoulder in the first and second positions.

4. The assembly of claim 3, wherein the inner shoulder is spaced apart from the outer shoulder by between about 30 cm and about 60 cm in the first position, and between about 0 cm and about 30 cm in the second position.

5. The assembly of claim 1, wherein the outer shoulder moves by between about 25 cm and about 35 cm relative to the inner shoulder when moving from the first position to the second position.

6. The assembly of claim 1, wherein the outer shoulder tapers conically in the distal direction.

7. The assembly of claim 1, further comprising the stent coupled to the stent engagement portion, wherein a cross-sectional profile of the stent engagement portion and the stent is less than the second diameter of the sheath lumen to permit travel of the stent engagement portion and the stent within the sheath distal section.

8. The assembly of claim 1, wherein when the stent is coupled to the stent engagement portion, the core member does not extend distally of the stent.

9. An assembly for a medical device delivery system, the assembly comprising:

an introducer sheath having a sheath proximal section, a sheath distal section, and a sheath lumen, the sheath lumen having a first diameter in the sheath proximal section and a second diameter less than the first diameter in the sheath distal section, wherein the sheath proximal section has a length of at least 100 cm and the sheath distal section has a length of at least 30 cm, the sheath distal section having a substantially constant lumen diameter along its length;

a core member having a core member proximal section, a core member distal section, and a stent engagement portion at the core member distal section for coupling a stent thereto; and a catheter having a catheter proximal section, a catheter distal section, a catheter lumen, and a transition section between the catheter proximal and distal sections, at which the catheter lumen tapers down distally from a larger diameter to a smaller diameter, wherein the introducer sheath is configured to be advanced within the catheter lumen such that a distal end of the introducer sheath abuts the transition section of the catheter, wherein the distal end of the introducer sheath tapers conically in a distal direction and is configured to self-center along a longitudinal axis of the catheter when urged to contact with the transition section, and wherein the sheath lumen in the sheath distal section and the catheter lumen in the catheter distal section together form a common lumen having a substantially constant diameter, and wherein the core member distal section is configured to be positioned within the sheath lumen along the sheath distal section and proximal to the distal end of the introducer sheath in a first position, the core member being distally advanceable by between about 30 cm to about 60 cm from the first position such that the core member distal section extends beyond the distal end of the introducer sheath and beyond a distal end of the catheter in a second position in which the distal end of the introducer sheath abuts the transition section of the catheter.

10. The assembly of claim 9, wherein the introducer sheath further comprises an inner shoulder between the sheath proximal and distal sections, and the core member further comprises an outer shoulder between the core member proximal and distal sections, the core member being advanceable within the sheath distal section until the outer shoulder converges toward the inner shoulder until reaching the second position.

11. The assembly of claim 10, wherein the inner shoulder is spaced apart from the outer shoulder in the first and second positions.

12. The assembly of claim 10, wherein the outer shoulder moves by between about 25 cm and about 35 cm relative to the inner shoulder when moving from the first position to the second position.

13. The assembly of claim 9, wherein a cross-sectional profile of the core member distal section is less than the second diameter of the sheath lumen to allow the core member distal section and the stent supported thereon to be advanceable together within the sheath distal section.

14. The assembly of claim 9, further comprising the stent coupled to the stent engagement portion, wherein a cross-sectional profile of the stent engagement portion and the stent is less than the second diameter of the sheath lumen to permit travel of the stent engagement portion and the stent within the sheath distal section.

15. The assembly of claim 9, wherein when the stent is coupled to the stent engagement portion, the core member does not extend distally of the stent.

16. An assembly for a medical device delivery system, the assembly comprising:
   a catheter having a catheter proximal section, a catheter distal section, a catheter lumen, and a transition section between the catheter proximal and distal sections, the catheter lumen having a first diameter in the catheter proximal section and a second diameter less than the first diameter in the catheter distal section; and
   an introducer sheath having a sheath proximal section, a sheath distal section including a distal end portion, and a sheath lumen, the sheath lumen having a third diameter in the sheath proximal section and a fourth diameter less than the third diameter in the sheath distal section, wherein the sheath proximal section has a length of at least 100 cm and the sheath distal section has a length of at least 30 cm, the sheath distal section having a substantially constant lumen diameter, wherein the introducer sheath is configured to be advanced within the catheter lumen such that the distal end portion of the introducer sheath contacts the transition section of the catheter, wherein the distal end portion of the introducer sheath tapers conically, in a distal direction and is configured to self-center along a longitudinal axis of the catheter when urged into contact with the transition section, and wherein the sheath lumen in the sheath distal section and the catheter lumen in the catheter distal section together form a common lumen having a substantially constant diameter.

17. The assembly of claim 16, wherein the distal end portion of the introducer sheath has a tapered shape, and the transition section has a conical shape configured to mate with the tapered shape of the distal end portion.

18. The assembly of claim 16, wherein the distal end portion of the introducer sheath has a greater rigidity than a remaining portion of the introducer sheath proximal to the distal end portion.

19. The assembly of claim 16, further comprising a core member having a core member proximal section and a core member distal section, wherein, when the distal end portion of the introducer sheath is in contact with the transition section of the catheter, the core member is advanceable within the sheath lumen such that the core member distal section is positioned within the catheter distal section.

* * * * *